United States Patent [19]

Mohamadi et al.

[11] Patent Number: 5,169,860
[45] Date of Patent: Dec. 8, 1992

[54] ANTITUMOR COMPOSITIONS AND METHODS OF TREATMENT

[75] Inventors: Fariborz Mohamadi; Michael M. Spees, both of Indianapolis, Ind.

[73] Assignee: Eli Lilly and Company, Indianapolis, Ind.

[21] Appl. No.: 850,531

[22] Filed: Mar. 13, 1992

[51] Int. Cl.$^5$ .................. A61K 31/38; A61K 31/40; C07D 333/34
[52] U.S. Cl. .................. 514/415; 514/418; 514/443; 514/470; 549/51; 549/53; 549/466; 549/467; 548/484; 548/486; 548/503; 548/504; 548/507
[58] Field of Search ............ 549/51, 53, 466, 467; 548/484, 486, 503, 504, 507; 514/483, 470, 418, 415

[56] References Cited

U.S. PATENT DOCUMENTS

| | | | |
|---|---|---|---|
| 3,083,207 | 3/1963 | Hoehn et al. | 540/606 |
| 3,097,242 | 7/1963 | Hoehn et al. | 564/34 |
| 3,102,115 | 8/1963 | Breuer et al. | 549/62 |
| 3,102,121 | 8/1963 | Breuer et al. | 548/90 |
| 3,736,122 | 5/1973 | Tung et al. | 71/103 |
| 3,849,110 | 11/1974 | Soper et al. | 71/103 |
| 4,845,128 | 7/1989 | Harper et al. | 514/592 |

FOREIGN PATENT DOCUMENTS

| | | |
|---|---|---|
| 1208561 | 7/1986 | Canada . |
| 107214 | 9/1983 | European Pat. Off. . |
| 166615 | 1/1986 | European Pat. Off. . |
| 222475 | 5/1987 | European Pat. Off. . |
| 291269 | 11/1988 | European Pat. Off. . |
| 1240866 | 6/1961 | Fed. Rep. of Germany . |
| 1144259 | 2/1963 | Fed. Rep. of Germany . |

OTHER PUBLICATIONS

W. J. Ehlhardt, Drug Metabolism and Disposition, 19:370 (1991).
J. J. Howbert et al., Synthetic Communications, 20:3193 (1990).
W. J. Ehlhardt, Drug Metabolism and Disposition, 19:366 (1991).
J. J. Howbert et al., Journal of Medicinal Chemistry, 33:2393 (1990).
G. B. Grindey et al., Proceedings of the American Association of Cancer Research, 27:277 (Abstract 1099) (1986).
C. W. Taylor et al., Journal of Clinical Oncology, 7:1733 (1989).
J. D. Hainsworth et al. Cancer Research, 49:5217 (1989).
R. Levine, Diabetes Care, 7 (Suppl. 1):3–7 (1984).
G. F. Holland et al., Journal of Medicinal and Pharmaceutical Chemistry, 3:99 (1961).
P. J. Houghton et al., Cancer Chemotherapy and Pharmacology, 25:84 (1989).
P. J. Houghton et al., Cancer Research, 50:318 (1990).
P. J. Houghton et al., Cancer Research, 50:664 (1990).
P. J. Houghton et al., Biochemical Pharmacology, 39:1187 (1990).
P. H. Dhahir et al., In Proceedings of the 36th ASMS Conference on Mass Spectroscopy and Allied Topics, pp. 972–973 (1988).
G. F. Holland, Journal of Organic Chemistry, 26:1662 (1961).
Chemical Abstracts, 52:17180; citing Haack et al., East German Patent 9688, Apr. 21, 1955.
F. Kurzer, Chemical Reviews, 50:1 (1952).
G. B. Grindey et al., In Proceedings of the American Association for Cancer Research, 28:309 (Abstract 1224) (1987).
H. Breuer et al., Chimie Therapeutique, Nov.-/Dec.(1973) 659.
L. J. Lerner et al., Metabolism, 14:578 (1965).

*Primary Examiner*—Richard L. Raymond
*Assistant Examiner*—Mark W. Russell
*Attorney, Agent, or Firm*—Nancy J. Harrison; Leroy Whitaker

[57] ABSTRACT

This invention provides the use of certain benzofuransulfonamide, benzothiophenesulfonamide, and indolesulfonamide derivatives in the treatment of susceptible neoplasms in mammals. Also provided are certain novel benzofuransulfonamide and benzothiophenesulfonamide derivatives and their pharmaceutical formulations.

34 Claims, No Drawings

ANTITUMOR COMPOSITIONS AND METHODS OF TREATMENT

BACKGROUND OF THE INVENTION

In recent years fundamental advances have been made in the development of chemical agents and regimens of therapy to combat neoplastic diseases. Despite these continuing advances, cancers continue to exact intolerable levels of human pain and suffering. The need for new and better methods of treating neoplasms and leukemias continues to fuel efforts to create new classes of compounds, especially in the area of inoperable or metastatic solid tumors, such as the various forms of lung cancer. Of the one million new cases of cancer diagnosed in the United States each year, more than 90% represent non-hematopoetic tumors, where improvements in five-year survival rates have been modest, at best. B. E. Henderson, et al.. Science. 254:1131-1137 (1991).

The recent avalanche of information regarding the basic biological processes involved in neoplasms has led to a deeper understanding of the heterogeneity of tumors. Ongoing work has led to the realization that individual tumors may contain many subpopulations of neoplastic cells that differ in crucial characteristics such as karyotype, morphology, immunogenicity, growth rate, capacity to metastasize, and response to antineoplastic agents.

It is because of this extreme heterogeneity among populations of neoplastic cells that new chemotherapeutic agents should have a wide spectrum of activity and a large therapeutic index. In addition, such agents must be chemically stable and compatible with other agents. It is also important that any chemotherapeutic regimen be as convenient and painless as possible to the patient This invention reports a series of sulfonylureas that are useful in the treatment of solid tumors. These compounds are orally active—which, of course, results in less trauma to the patient—and are relatively non-toxic. These compounds also have an excellent therapeutic index. The compounds and their formulations are novel.

Many sulfonylureas are known in the art. Certain of these compounds are known to have hypoglycemic activities, and have been used medicinally as such agents. In addition, sulfonylureas have been taught to have herbicidal and antimycotic activities. General reviews of compounds of this structural type are taught by Kurzer, Chemical Reviews. 50:1 (1952) and C. R. Kahn and Y. Shechter, Goodman and Gilman's. The Pharmacological Basis of Therapeuutics. (Gilman, et al. 8th ed. 1990) 1484-1487. Some diarylsulfonylureas have been reported as being active antitumor agents. e.g. U.S. Pat. No. 4,845,128 of Harper, et al. (1989); European Patent Publication 0222475 (published May 20, 1987); European Patent Publication 0291269 (published Nov. 17, 1988); European Patent Publication 0467613 (published Jan. 22, 1992); Grindey, et al.. American Association of Cancer Research, 27:277 (1986); and Houghton, et al., Cancer Chemotherapy and Pharmacology, 25:84-88 (1989).

SUMMARY OF THE INVENTION

This invention provides a method of treating susceptible neoplasms in mammals which comprises administering to a mammal in need of said treatment an oncolytically effective amount of a compound of Formula I:

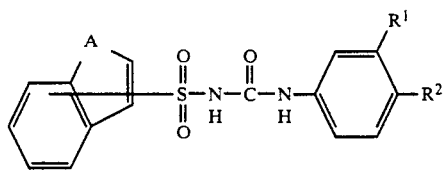

wherein:
A is —S—, —NH— or —O—;
$R^1$ is halo, $C_1$-$C_3$ alkyl, or hydroqen; and
$R^2$ is halo, $C_1$-$C_3$ alkyl, or trifluoromethyl; or a pharmaceutically acceptable salt or solvate thereof.

This invention also provides novel compounds of Formula II

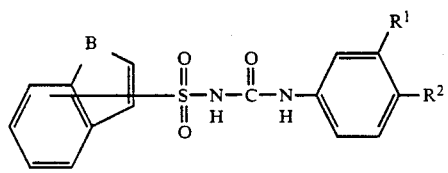

wherein
B is —S—, or —O—;
$R^1$ is halo, $C_1$-$C_3$ alkyl, or hydrogen; and
$R^2$ is halo, $C_1$—$C_3$ alkyl, or trifluoromethyl; or a pharmaceutically acceptable salt or solvate thereof. Such compounds are especially preferred in the treatment of susceptible neoplasms in mammals.

In addition, this invention provides pharmaceutical formulations comprising an effective amount for treating susceptible neoplasms of a compound of Formula II, in combination with a suitable pharmaceutical carrier, diluent, or excipient. These formulations are useful in the treatment of mammals suffering from susceptible neoplasms.

DETAILED DESCRIPTION AND PREFERRED EMBODIMENTS

As used herein, the term "halo" refers to fluoro, chloro, bromo, and iodo.

Preferred methods of treatment employ compounds of Formula I in which $R^1$ is chloro, fluoro, bromo, methyl, ethyl, or hydrogen; and $R^2$ is chloro, fluoro, bromo, methyl, ethyl, or trifluoromethyl.

Preferred compounds of the instant invention are those of Formula II in which $R^1$ is chloro, fluoro, bromo, methyl, ethyl, or hydrogen; and $R^2$ is chloro, fluoro, bromo, methyl, ethyl, or trifluoromethyl.

Illustrative compounds falling within the scope of Formula I are:
N-[[(4-chlorophenyl)amino]carbonyl]-1H-indole-5-sulfonamide;
N-[[(3,4-dichlorophenyl)amino]carbonyl]benzo[B]thiophene-3-sulfonamide;
N-[[4-fluorophenyl)amino]carbonyl]-2-benzofuransulfonamide; N-[[(3,4-dibromophenyl)amino]carbonyl]-2-benzofuransulfonamide;
N-[[(3,4-difluorophenyl)amino]carbonyl]-3-benzofuransulfonamide; sulfonamide;
N-[[(4-methylphenyl)amino]carbonyl]-1H-indole-6-sulfonamide;

N-[[(4-chlorophenyl)amino]carbonyl]benzo[B]thiophene-5-sulfonamide;
N-[[(3,4-dichlorophenyl)amino]carbonyl]-5-benzofuransulfonamide;
N-[[(4-chlorophenyl)amino]carbonyl]-5-benzofuransulfonamide;
N-[[(4-chlorophenyl)amino]carbonyl]-6-benzofuransulfonamide;
N-[[(3,4-difluorophenyl)amino]carbonyl]-1H-indole-4-sulfonamide;
N-[[(4-chlorophenyl)amino]carbonyl]-1H-indole-6-sulfonamide;
N-[[(3-methyl-4-chlorophenyl)amino]carbonyl]benzo[B]thiophene-2-sulfonamide;
N-[[(3-chloro-4-trifluoromethylphenyl)amino]carbonyl]-1H-indole-5-sulfonamide;
N-[[(4-trifluoromethylphenyl)amino]carbonyl]-3-benzofuransulfonamide;
N-[[(4-trifluoromethylphenyl)amino]carbonyl]benzo[B]thiophene-2-sulfonamide;
N-[[(3-bromo-4-trifluoromethylphenyl)amino]carbonyl]-5-benzofuransulfonamide;
N-[[(3,4-dimethylphenyl)amino]carbonyl]-5-benzofuransulfonamide;
N-[[(4-ethylphenyl)amino]carbonyl]benzo[B]thiophene-2-sulfonamide;
N-[[(3-methyl-4-trifluoromethylphenyl)amino]carbonyl]-1H-indole-5-sulfonamide.

The compounds of Formulas I and II are generally referred to as derivatives of N-[[(substituted phenyl)amino]carbonyl]-benzofuransulfonamides, -indolesulfonamides, and -benzothiophenesulfonamides. Alternatively, the compounds can be referred to as 1- and -substituted sulfonylureas or N- and N'-substituted sulfonylureas.

The compounds of formulas I and II can be prepared by methods known in the literature. Generally, these methods involve either the reaction of a sulfonamide with an isocyanate or a reaction of a sulfonylcarbamate with an appropriately-substituted aniline.

A preferred process for preparing a compound of Formula I comprises reacting a sulfonylisocyanate of Formula III

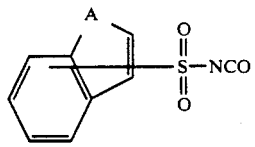
III with an aniline derivative of Formula IV

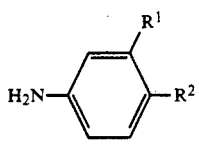
IV where A, $R^1$ and $R^2$ are the same as previously defined, generally in the presence of a base. Any suitable basic material can be used such as sodium hydroxide, potassium hydroxide, lithium hydroxide, sodium methoxide, sodium hydride and the like.

The reaction between compounds III and IV is usually performed using equimolar amounts of the two reactants, although other ratios are operative. The reaction is preferably carried out in a solvent which is non-reactive under the reaction conditions such as benzene, toluene, acetonitrile, diethyl ether, tetrahydrofuran, dioxane, methylene chloride, or most preferably acetone.

The reaction can be carried out at temperatures from about 0° C. up to about 100° C. At the preferred temperature range of from about 20° C. to about 30° C., the reaction produces a strong exotherm and the reaction is usually complete within one hour The product thus obtained is recovered by filtration and can be purified, if desired, by any number of methods known to those skilled in the art, such as chromatography or crystallization An alternative process for preparing a compound of Formula I comprises reacting an appropriately substituted sulfonamide of Formula V

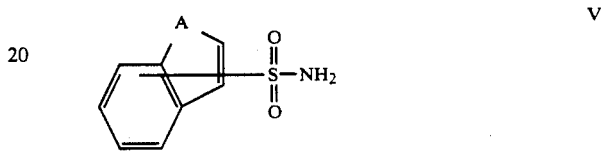
V with an isocyanate of Formula VI

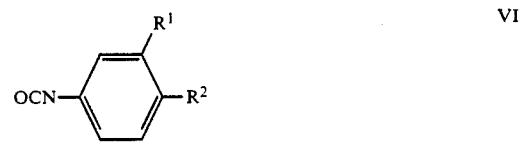
VI to provide the corresponding compound of Formula I.

The reaction is generally performed in a mixture of water and a water-miscible, non-reactive solvent such as tetrahydrofuran or acetone in the presence of an acid scavenger such as sodium hydroxide, potassium hydroxide, lithium hydroxide, sodium methoxide, sodium hydride and the like. Generally, an equimolar or slight molar excess of VI is employed, although other ratios are operative. Usually, the amount of base used is approximately equimolar to the amount of V. The reaction is generally carried out from C up to about 100° C. At the preferred temperature C to about 30° C., the reaction is usually complete within about three hours A preferred process for preparing a compound of Formula I involves reacting a sulfonamide of Formula V with an alkyl haloformate of the formula $XCOOR^3$. where X is bromo or chloro and $R^3$ is $C_1$-$C_3$ alkyl, to provide the carbamate of Formula VII and then reacting it with an aniline derivative of Formula IV to provide the corresponding product I

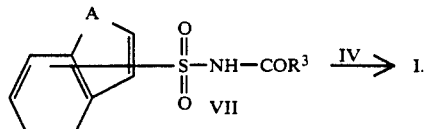

The transformation of V into VII is usually accomplished in a non-reactive solvent, such as acetone or methyl ethyl ketone, in the presence of an acid scavenger, such as an alkali metal carbonate, for example potassium carbonate. A molar excess of the haloformate is usually added, although other ratios are operative. The reaction mixture is heated to a temperature from about 30° C. up to the reflux temperature of the mixture for a period of about 1-6 hours to provide the desired intermediate VII. Intermediate carbamate VII and the substituted aniline IV are then heated together in an inert high-boiling solvent, such as dioxane, toluene, or diglyme, at temperatures from about 0° C. up to the reflux temperature of the mixture to provide the desired product I.

Intermediates II, IV, V, and VI and any other reagents required for other methods of preparation, are commercially available, are known in the literature, or can be prepared by methods known in the art.

This invention includes methods employing the pharmaceutically acceptable salts of the Formula I compounds and the pharmaceutically acceptable salts of the Formula II compounds. The Formula I and II compounds can react with basic materials such as alkali metal- or alkaline earth metal hydroxides, carbonates, and bicarbonates including, without limitation, sodium hydroxide, sodium carbonate, potassium hydroxide, calcium hydroxide, lithium hydroxide, etc. to form pharmaceutically acceptable salts such as the corresponding sodium, potassium, lithium, or calcium salt. Organic bases can also be used, including primary, secondary, and tertiary alkyl amines such as methylamine, triethylamine, and the like.

This invention further relates to the pharmaceutically acceptable solvates of the compounds of Formulas I and II. The Formula I and II compounds can react with solvents such as water, methanol, ethanol and acetonitrile to form pharmaceutically acceptable solvates such as the corresponding hydrate, methanolate, ethanolate and acetonitrilate.

The terms and abbreviations used in the instant examples have their normal meanings unless otherwise designated. For example "° C." refers to degrees Celsius; "N" refers to normal or normality; "mmole" refers to millimole; g" refers to gram; .mL" means milliliter; "M" refers to molar or molarity; and .NMR" refers to nuclear magnetic resonance.

The following examples further illustrate the preparation of the compounds of Formula I. These examples are illustrative only and are not intended to limit the scope of the invention in any way.

Method A for the Synthesis of Sulfonylurea from Sulfonamide

To a solution of sulfonamide (7.2 mmol) dissolved in 10 mL of acetone was added 1 N aqueous sodium hydroxide (7.2 mL, 7.2 mmol). The mixture was stirred at room temperature for 10 minutes. A solution of the arylisocyanate (7.2 mmol) dissolved in 10 mL of acetone was added dropwise to this mixture. The reaction was stirred overnight, then acidified with 7.2 mL (7.2 mmol) of 1 N aqueous hydrochloric acid. The precipitated N-aryl-N'-arylsulfonylurea was filtered under vacuum and purified by flash chromatography. W. C. Still, et al.. *Journal of Organic Chemistry*, 43:2923 (1978).

Method B for the Synthesis of Sulfonylurea from Sulfonamide

The sulfonamide (5.74 mmol) and potassium t-butoxide (5.74 mmol; were stirred in 20 mL of acetone for 30 minutes. To this mixture was added arylisocyanate (5.74 mmol), and the reaction was stirred for 3 hours. The reaction mixture was added dropwise to 100 mL of 0.5 N hydrochloric acid and stirred for 2 hours. The aqueous layer was extracted with toluene (2×100 mL). The combined organic layer was dried with anhydrous sodium sulfate, filtered, and concentrated under vacuum. The N-aryl-N'-arylsulfonylurea was filtered under vacuum and purified by flash chromatography. The flash chromatography was performed as described in W. C. Still, et al.. *Journal of Organic Chemistry*, 43:2923 (1978).

EXAMPLE 1

Preparation of N-[[(4-chlorophenyl)amino]carbonyl]-2-benzofuransulfonamide

To a solution of benzofuran (4.55 g, 38.5 mmol) in 100 mL of anhydrous tetrahydrofuran under a nitrogen atmosphere at −78° C. was added a 1.3 M hexanes solution of n-butyllithium (29.6 mL, 38.5 mmol). The reaction was warmed to 0° C. and stirred for 30 minutes. Sulfur dioxide gas was bubbled through this mixture for 20 minutes at 0° C. and the reaction was concentrated under vacuum. The residue was dissolved in 100 mL of water, to which were added 304 millimoles of sodium acetate and 100 millimoles of hydroxylamine-0-sulphonic acid. This reaction was stirred at room temperature for 1.5 hours. The mixture was diluted with 200 mL of water, and the aqueous layer was separated and poured into 600 mL of diethyl ether. The ether layer was extracted with 1 N sodium hydroxide (3×100 mL). The combined aqueous extract was acidified with about 300 mL of 1 N hydrochloric acid, and then extracted with methylene chloride. The combined methylene chloride extract was dried with anhydrous sodium sulfate, filtered, and concentrated under vacuum to provide 2.3 g of 2benzofuransulfonamide. The sulfonamide (11.7 mmol) was reacted with 4-chlorophenylisocyanate (11.7 mmol) as described in Method A above to obtain 2 grams of the title product as a solid. $^1$H NMR (CD$_3$SOCD$_3$); δ9.23 (s, 1 H), 7.87 (d, J=9 Hz, 1 H), 7.82 (s, 1 H), 7.78 (d, J=9 Hz, 1 H), 7.58 (dd, J=9, 9 Hz, 1 H), 7.46 (m, 1 H), 7.44 (d, J=9 Hz, 2 H), 7.32 (d, J=9 Hz, 2 H).

Analysis for C$_{15}$H$_{11}$ClN$_2$O$_4$S:
Theory: C, 51.36; H, 3.16; N, 7.99.
Found: C, 51.39; H, 3.25; N, 7.89.

EXAMPLE 2

Preparation of N-[[(4-methylphenyl)amino]carbonyl]-2-benzofuransulfonamide

2-Benzofuransulfonamide (7.6 mmol), prepared as described in Example 1, was reacted with 4-methylphenylisocyanate (7.6 mmol) as described in Method A to obtain 1.6 g of the title product as a solid. $^1$H NMR (CD$_3$SOCD$_3$): δ8.91 (s, 1 H), 7.87 (d, J =8 Hz, 1 H), 7.81 (s, 1 H), 7.76 (d, J =8 Hz, 1 H), 7.57 (dd, J =8, 8 Hz, 1 H), 7.42 (dd, J =8, 8 Hz, 1 H), 7.28 (d, J =9 Hz, 2 H), 7.07 (d, J =9 Hz, 2 H), 2.23 (s, 3 H). Analysis for C$_{16}$H$_{14}$N$_2$O$_4$S:
Theory: C, 58.70; H, 4.27; N, 8.48
Found: C, 58.45; H, 4.33; N, 8.471

EXAMPLE 3

Preparation of N-[[(3,4 dichlorophenyl)amino]carbonyl]-2-benzofuransulfonamide

2-Benzofuransulfonamide (7.6 mmol), prepared as described in Example 1, was reacted with 3,4-dichlorophenylisocyanate (7.6 mmol) as described in Method A to obtain 2.4 g of the title product as a solid. $^1$H NMR (CD$_3$SOCD$_3$): δ9.43 (s, 1 H), 7.88 (d, J =8 Hz, 1 H), 7.85 (s, 1 H), 7.80 (m, 1 H), 7.76 (m, 1 H), 7.59 (dd, J =6, 8 Hz, 1 H), 7.52 (d, J =8 Hz, 1 H), 7.45 (dd, J =6, 8 Hz, 1 H), 7.35 (dd, J =3, 6 Hz, 1 H).

Analysis for $C_{15}H_{10}Cl_2N_2O_4S$:
Theory: C, 46.77; H, 2.63; N, 7.27.
Found: C, 46.78; H, 2.63; N, 7.24.

EXAMPLE 4

Preparation of N-[[(4-bromophenyl)amino]carbonyl]-2-benzofuransulfonamide

2-Benzofuransulfonamide (7.6 mmol), prepared as described in Example 1, was reacted with 4-bromophenylisocyanate (7.6 mmol) as described in Method A to obtain 2.3 g of the title product as a solid. $^1$H NMR ($CD_3SOCD_3$): δ9.35 (s, 1 H), 7.87 (d, J =8 Hz, 1 H), 7.82 (s, 1 H), 7.78 (d, J =8 Hz, 1 H), 7.58 (dd, J =8, 8 Hz, 1 H), 7.46 (d, J =9 Hz, 2 H), 7.44 (dd, J =8, 8 Hz, 1 H), 7.38 (d, J =9 Hz, 2 H).

Analysis for $C_{15}H_{11}BrN_2O_4S$:
Theory: C, 45.59; H, 2.81; N, 7.09.
Found: C, 45.34; H, 2.85; N, 6.89.

EXAMPLE 5

Preparation of N-[[(4-chlorophenyl)amino]carbonyl]-4-benzofuransulfonamide

The allyl ether of 3-bromophenol (29.8 g, 130 mmol) was refluxed overnight in 100 mL of N-methylpyrrolidinone. The reaction was cooled to room temperature, added to 500 mL of ice water and extracted with ether (3×200 mL). The combined organic layer was extracted with brine (2×100 mL), dried over anhydrous sodium sulfate, filtered, and concentrated under vacuum. Purification was performed using a preparative high pressure liquid chromatogram (Waters Prep 500 A), eluting with a gradient of 0–10% ethyl acetate in a hexanes solution on two silica gel cartridges. This purification provided 11.5 g of 2-(3-allyl)-5-bromophenol ($R_f$=0.41) and 14.7 g of 2-(3-allyl)-3-bromophenol ($R_f$=0.32).

An aliquot of 2-(3-allyl)-3-bromophenol (6.0 g, 8.2 mmol) was dissolved in 125 mL of methylene chloride and ozonized at −78° C. The reaction was purged at −78° C. with a stream of nitrogen. Dimethyl sulfide (6 mL) was then added and this admixture was stirred at room temperature for 1 hour. The mixture was concentrated under vacuum, then added to a solution of polyphosphoric acid (10 g) suspended in 200 mL of toluene. This mixture was refluxed for 2.5 hours and then added to ice water. The organic layer was separated, dried with anhydrous sodium sulfate, filtered, and concentrated under vacuum. Flash chromatography with pentane provided 3.2 g of 4-bromobenzofuran.

The 2-position of the 4-bromobenzofuran (3.2 g) was protected with a trimethylsilyl group by first reacting the 4-bromobenzofuran with lithium diisopropylamide in the presence of tetrahydrofuran at −78° C. This is followed by the addition of trimethylsilylchloride to provide 2.3 g of 2-trimethylsilyl-4-bromobenzofuran. Metallation of the 2-trimethylsilyl-4-bromobenzofuran, followed by sulfur dioxide trapping using hydroxylamine-0-sulphonic acid, as described for the synthesis of 2-benzofuransulfonamide in Example 1, provided 1.1 g of 2-trimethylsilyl-4-benzofuransulfonamide. Desilylation was achieved with a 1.0 M tetrahydrofuran solution of tetrabutylammonium fluoride (2.5 equivalents) to produce 0.66 g of 4-benzofuransulfonamide.

The 4-benzofuransulfonamide (3.4 mmol) was reacted with 4-chlorophenylisocyanate (3.4 mmol), as described in Method B above, to obtain 1.0 g of the title product as a solid. $^1$H NMR ($CD_3SOCD_3$): δ10.12 (bs, 1 H), 8.96 (s, 1 H), 8.26 (d, J =3 Hz, 1 H), 7.98 (d, J =9 Hz, 1 H), 7.92 (d, J =9 Hz, 1 H), 7.56 (dd, J =9, 9 Hz, 1 H), 7.36 (d, J =9 Hz, 2 H), 7.34 (d, J =3 Hz, 1 H), 7.28 (d, J =9 Hz, 2 H). Analysis for $C_{15}H_{11}ClN_2O_4S$:
Theory: C, 51.36; H, 3.16; N, 7.97.
Found: C, 51.66; H, 3.70; N, 7.66.

EXAMPLE 6

Preparation of N-[[(4-chlorophenyl)amino]carbonyl]-5-benzofuransulfonamide hemihydrate To a solution of 5-bromobenzofuran (4.7 g, 23.8 mmol),dissolved in 100 mL of anhydrous tetrahydrofuran at −78° C. under a nitrogen atmosphere, was added 15.0 mL of a 1.6 M hexanes solution of n-butyllithium (23.8 mmol). The reaction was warmed to 0° C. and stirred for 15 minutes. Sulfur dioxide gas was bubbled through this mixture for 20 minutes at 0° C. and the reaction concentrated under vacuum. The residue was dissolved in 250 mL of water. To this solution were added 15.6 g (190 mmol) of sodium acetate and 8.3 g (73.7 mmol) of hydroxylamine-0-sulphonic acid. This reaction was stirred at room temperature for 1.5 hours. The solution was extracted with diethyl ether (2×150 mL). The combined organic layer was dried with anhydrous magnesium sulfate, filtered, and concentrated under vacuum. Flash chromatography of the residue with 18% ethyl acetate/hexanes on silica gel provided 2.3 g (10.0 mmol) of 5-benzofuransulfonamide. The 5-benzofuransulfonamide was reacted with 4-chlorophenylisocyanate (10.0 mmol), as described in Method A above, to obtain 1.4 g of the title product as a solid. $^1$H NMR ($CD_3SOCD_3$): δ0.62 (bs, 1 H), 9.02 (s, 1 H), 8.38 (d, J =2 Hz, 1 H), 8.20 (d, J =2Hz, 1 H), 7.96 (dd, J =2, 9 Hz, 1 H), 7.86 (d, J =9 Hz, 1 H), 7.38 (d, J =9 Hz, 2 H), 7.30 (d, J =9 Hz, 2 H), 7.20 (d, J =2 Hz, 1 H).

Analysis for $C_{15}H_{11}ClN_2O_4S \cdot \frac{1}{2}H_2O$:
Theory: C, 50.07; H, 3.36; N, 7.79.
Found: C, 49.96; H, 3.15; N, 7.61.

EXAMPLE 7

Preparation of N-[[(4-methylphenyl)amino]carbonyl]-5-benzofuransulfonamide

The 5-benzofuransulfonamide (5.74 mmol) and 4-methylphenylisocyanate (5.74 mmol) were reacted as described in Method B above to obtain a solid. This residue was purified by reverse phase chromatography with 50% acetonitrile in water with 1% acetic acid on a C18 column to obtain 0.64 g of the title product as a solid. $^1$H NMR ($CD_3SOCD_3$): κ10.35 (bs, 1 H), 8.74 (s, 1 H), 8.38 (d, J =3 Hz, 1 H), 8.20 (d, J =3 Hz, 1 H), 7.96 (dd, J =3, 9 Hz, 1 H), 7.86 (d, J =9 Hz, 1 H), 7.22 (d, J =9 Hz, 2 H), 7.20 (d, J =3 Hz, 1 H), 7.06 (d, J =9 Hz, 2 H), 2.22 (s, 3 H).

Analysis for $C_{16}H_{14}N_2O_4S$:
Theory: C, 58.17; H, 4.27; N, 8.48.
Found: C, 57.87; H, 4.38; N, 8.26.

EXAMPLE 8

Preparation of N-[[(4-chlorophenyl)amino]carbonyl]-6-benzofuransulfonamide

An aliquot of 2-(3-allyl)-5-bromophenol (11.5 g, 68.8 mmol) was dissolved in 300 mL of methylene chloride and ozonized at −78° C. The reaction was purged at -78° C. with a stream of nitrogen. Fifteen milliliters of dimethyl sulfide were added and the reaction stirred at room temperature for 1 hour. The mixture was concentrated under vacuum, then added to a solution of polyphosphoric acid (21 g) suspended in 300 mL of toluene. This mixture was refluxed for 2.5 hours, and added to ice water. The organic layer was separated, dried with anhydrous sodium sulfate, filtered, and concentrated under vacuum. Flash chromatography with pentane provides 3.8 g of 6-bromobenzofuran.

The 2-position of the 6-bromobenzofuran (3.8 g) was protected with a trimethysilyl group as described in Example 5, to provide 2.4 g of 2-trimethylsilyl-6-bromobenzofuran. followed by sulfur dioxide trapping with hydroxylamine-0-sulphonic acid, as described for the synthesis of 2-benzofuransulfonamide in Example 1, provided 1.1 g of 2-trimethylsilyl-6-benzofuransulfonamide. Desilylation was achieved by adding 2.5 equivalents of a solution of 1.0 M tetrabutylammonium fluoride in tetrahydrofuran to produce 0.52 g of 6-benzofuransulfonamide.

The 4-benzofuransulfonamide (2.6 mmol) was reacted with 4-chlorophenylisocyanate (2.6 mmol) as described in Method B above to obtain 0.7 g of the title product as a solid. $^1$H NMR (CD$_3$SOCD$_3$): δ9.00 (s, 1 H), 8.26 (d, J =4 Hz, 1 H), 8.14 (s, 1 H), 7.86 (d, J =8 Hz, 1 H), 7.82 (d, J =8 Hz, 1 H), 7.32 (d, J =9 Hz, 2 H), 7.26 (d, J =9 Hz, 2 H), 7.10 (d, J =4 Hz, 1 H).

Analysis for C$_{15}$H$_{11}$ClN$_2$O$_4$S:
 Theory: C, 51.36; H, 3.16; N, 7.97.
 Found: C, 51.65; H, 3.14; N, 7.75.

EXAMPLE 9

Preparation of N-[[(4-chlorophenyl)amino]carbonyl]-1H-indole-2-sulfonamide

The procedure of Method A was followed in that -indolesulfonamide (10.2 mmol) was reacted with 4-chlorophenylisocyanate (10.2 mmol) to obtain 2.1 g of title product as a solid. The 2-indolesulfonamide was prepared by procedures well known in the art. See, e.g., European Patent Application 070698 (published Jan. 26, 1983). $^1$H NMR (CD$_3$SOCD$_3$): δ12.14 (s, 1 H), 10.82 (bs, 1 H), 9.07 (s, 1 H), 7.73 (d, J =8 Hz, 1 H), 7.56 (d, J =8 Hz, 1 H), 7.43 (d, J =9 Hz, 2 H), 7.34 (d, J =9 Hz, 2 H), 7.32 (m, H), 7.19 (m, 1 H), 7.15 (dd, J =6, 8 Hz, 1 H).

Analysis for C$_{15}$H$_{12}$ClN$_3$O$_3$S:
 Theory: C, 51.51; H, 3.46; N, 12.01.
 Found: C, 51.22; H, 3.46; N. 11.83.

EXAMPLE 10

Preparation of N-[[(4-chlorophenyl)amino]carbonyl]-1H-indole-6-sulfonamide

To a solution of 4-chloro-3-nitrophenylsulfonamide (12 g, 51 mmol) dissolved in 50 mL of anhydrous dimethylformamide, was added 13.1 g (116 mmol) of ethylcyanoacetate and 10.5 g (76 mmol) of anhydrous potassium carbonate. This mixture was heated at 110° C. for 3 hours, cooled to room temperature, and added to ice water containing 8 mL of concentrated sulfuric acid. The mixture was extracted with ethyl acetate (3×200 mL), and the combined organic layer was back extracted with 200 mL of water. The organic layer was dried over anhydrous sodium sulfate, filtered, and concentrated under vacuum. Purification by a preparative high pressure liquid chromatogram (Waters Prep 500 A) with 55% ethyl acetate in hexanes on a silica gel cartridge. The product was added to 45 mL of 50% aqueous acetic acid containing 3 mL of concentrated sulfuric acid and refluxed for 12 hours. The reaction was cooled to room temperature and added to 400 mL water. This mixture was extracted with ethyl acetate (3×100 mL). The combined organic layer was dried with anhydrous sodium sulfate, filtered, and concentrated under vacuum. The residue was crystallized from 40 mL of ethyl acetate, 3 mL of ethanol and 1 mL of hexanes to obtain 6.9 g of 3-nitro-4-(2-acetonitrile)phenyl sulfonamide. This material was dissolved in 40 mL of ethanol containing 3 g of 5% palladium on activated carbon. This mixture was placed in a Parr Hydrogenation apparatus with 60 p.s.i. of hydrogen at 40° C. for 3 hours. This mixture was filtered, the filtrate concentrated under vacuum, and the residue recrystallized from 20 mL of ethyl acetate and 10 mL of ethanol to obtain 2.4 g of 6-indolesulfonamide. The sulfonamide (6.1 mmol) was reacted with 4-chlorophenylisocyanate (6.1 mmol) as described in Method A above to obtain 1.1 g of the title product as a solid. $^1$H NMR (CD$_3$SOCD$_3$): δ11.68 (s, 1 H), 8.90 (s, 1 H), 8.10 (d, J =2 Hz, 1 H), 7.72 (d, J =9 Hz, 1 H), 7.66 (d, J =3 Hz, 1 H), 7.58 (dd, J =3, 9 Hz, 1 H), 7.40 (d, J =9 Hz, 2 H), 7.28 (d, J =9 Hz, 2 H), 6.60 (d, J =2 Hz, 1 H). Analysis for C$_{15}$H$_{12}$ClN$_3$O$_3$S:
 Theory: C, 51 51; H, 3.46; N, 12.01.
 Found: C, 51.24; H, 3.67; N, 11.72.

EXAMPLE 11

Preparation of N-[[(4-chlorophenyl)amino]carbonyl]-benzo[B]thiophene-2-sulfonamide To a solution of 13.4 g (100 mmol) of benzothiophene, dissolved in 50 mL anhydrous diethyl ether, was added 62.5 mL of a 1.6 M hexanes solution of n-butyllithium (100 mmol) The reaction mixture was refluxed for 4 hours and then cooled to about −20° C. Sulfuryl chloride (16.1 mL, 200 mmol) was added dropwise. This suspension was stirred at ambient temperature overnight and then added to 75 mL of ice water. The ether layer was dried over anhydrous sodium sulfate, filtered, and concentrated under vacuum. The residue was added to 100 mL of concentrated ammonium hydroxide and the suspension was warmed to 55° C. The solution was diluted with 200 mL of water and stirred at ambient temperature for several hours Product was collected by filtration under vacuum. The residue was suspended in 150 mL toluene and filtered to provide 9.2 g of 2-benzo[B]thiophenesulfonamide. The sulfonamide (25 mmol) was reacted with 4-chlorophenylisocyanate (27 mmol) as described in Method A above to obtain 8.7 g of the title product as a solid. $^1$H NMR (CD$_3$SOCD$_3$): δ9.12 (s, 1 H), 8.22 (s, 1 H), 8.10 (m, 2 H), 7.50 (m, 2 H), 7.44 (d, J =9 Hz, 2 H), 7.32 (d, J =9 Hz, 2 H).

Analysis for C$_{15}$H$_{11}$ClN$_2$O$_3$S$_2$:
 Theory: C, 49.11; H, 3.02; N, 7.64.
 Found: C, 49.36; H, 3.09; N, 7.54.

EXAMPLE 12

Preparation of N-[[(4-chlorophenyl)amino]carbonyl]-benzo[B]thiophene-3-sulfonamide 3-Benzo[B]thiophenesulfonamide (6.4 mmol) was reacted with 4-chlorophenylisocyanate (6.4 mmol) as described in Method A to obtain 1.1 g of the title product as a solid. $^1$H NMR (CD$_3$SOCD$_3$): δ10.94 (bs, 1 H), 8.99 (s, 1 H), 8.75 (s, 1 H), 8.27 (d, J =8 Hz, 1 H), 8.16 (d, J =8 Hz, 1 H), 7.60 (dd, J =8, 8 Hz, 1 H), 7.53 (dd, J =8, 8 Hz, 1 H), 7.38 (d, J =9 Hz, 2 H), 7.31 (d, J =9 Hz, 1 H).

Analysis for C$_{15}$H$_{11}$ClN$_2$O$_3$S$_2$:
 Theory: C, 49.11; H, 3.02; N, 7.64.
 Found: C, 48.42; H, 3.07; N, 7.28.

EXAMPLE 13

Preparation of N-[[(4-chlorophenyl)amino]carbonyl]-benzo[B]thiophene-5-sulfonamide To a solution of 5-bromobenzo[B]thiophene (9.4 mmol) in 100 mL of anhydrous tetrahydrofuran under a nitrogen atmosphere at −78° C. was added 5.9 mL of a 1.6 M hexanes solution of n-butyllithium (9.4 mmol). The 5bromobenzo[B]thiophene was synthesized by procedures well known in the art. See, European Patent Application 355827 (published Feb. 28, 1990). The reaction was warmed to 0° C. and stirred for 30 minutes. Sulfur dioxide gas was bubbled through this mixture for 20 minutes at 0° C., and the reaction concentrated under vacuum. The residue was dissolved in 50 mL of water. Sodium acetate (74 mmol) and hydroxylamine-O-sulphonic acid (24 mmol) were added to this solution and this reaction was stirred at room temperature for 1.5 hours. This mixture was diluted with 50 mL of water and the reaction extracted with ether (3×50 mL). The combined organic layer was extracted with 1 N sodium hydroxide (3×50 mL), the organic layer discarded, and the aqueous layer acidified with about 150 mL of 1 N hydrochloric acid. The aqueous layer was extracted with methylene chloride (3×50 mL). The combined organic layer was dried with anhydrous sodium sulfate, filtered, and concentrated under vacuum. The residue was purified by flash chromatography with 30% acetone in hexanes with 1% acetic acid on silica gel to obtain 340 mg of 5benzo[B]thiophenesulfonamide. The sulfonamide (1.6 mmol) was reacted with 4-chlorophenylisocyanate (1.9 mmol) as described in Method A above to obtain 240 mg of the title product as a solid. $^1$H NMR (CD$_3$SOCD$_3$): δ9.04 (s, 1 H), 8.16 (s, 1 H), 8.08 (d, J =6 Hz, 1 H), 8.04 (d, J =6 Hz, 1 H), 7.52 (d, J =6 Hz, H), 7.46 (m, 2 H), 7.42 (d, J =9 Hz, 2 H), 7.30 (d, J =Hz, 2 H).

Analysis for C$_{15}$H$_{11}$ClN$_2$O$_3$S$_2$:
Theory: C, 49.11; H, 3.02; N, 7.64.
Found: C, 47.75; H, 3.18; N, 7.96.

The compounds of Formula I are antineoplastic agents and the invention provides a method of treating susceptible neoplasms in mammals which comprises administering to a mammal in need of said treatment an oncolytically effective amount of a compound of Formula I. In particular, the present compounds are useful in treating solid tumors including carcinomas such as ovarian, nonsmall cell lung, gastric, pancreatic, prostate, renal cell, breast, colorectal, small cell lung, melanoma, and head and neck; and sarcomas such as Kaposi s sarcoma and rhabdomyosarcoma.

The compounds of Formula I have been shown to be active against transplanted mouse tumors in The compounds were tested in C3H mice bearing a 6C3HED lymphosarcoma, also known as the Gardner lymphosarcoma (GLS). The 6C3HED lymphosarcoma was obtained from the Division of Cancer Treatment, National Cancer Institute, Tumor Bank, maintained at E. G. and G. Mason Research (Worcester, Massachusetts).

First passage tumor was stored in liquid nitrogen using standard techniques. The transplanted tumor was reestablished from the Tumor Bank every six months or as needed. The tumor was maintained by serial passage twice weekly in C3H mice.

In the procedures utilized here, the tumor was removed from passage animals and minced into 1- to 3-mm cubic fragments using sterile techniques. Tumor pieces were checked for sterility using both Antibiotic Medium 1 and Brain Heart Infusion (Difco, Detroit, Michigan). The tumor pieces were implanted into the recipient C3H mice subcutaneously in an auxillary site by trochar.

Drug therapy on the appropriate schedule was initiated seven days after tumor implantation. The compound being tested was mixed with 2.5% Emulphor EL620 from GAF Corporation (1:40 dilution in 0.9% saline). The total dosage volume for each administration was 0.5 mL. All animals were weighed at the beginning and end of administration of the subject compounds. Food and water were provided ad libitum Each control group and each dosage level of the treated groups generally consisted of 10 mice selected at random from the pool of implanted animals. The formulations were administered orally by gavage with the use of an 18-gauge needle. Compounds were dosed daily for 10 days.

The tumor was measured five days after treatment ended with two dimensional measurements (width and length) of the tumor taken using digital electronic calipers interfaced to a microcomputer. J. F. Worzalla, et al.. *Investicational New Drugs.* 8:241-251 (1990). Tumor weights were calculated from these measurements using the following formula:

Tumor weight (mg)=[tumor length (mm)×[tumor width (mm)]2]÷2

At least one control group of an equal number of mice was treated with the same volume of 2.5% Emulphor only. The percent inhibition was determined by subtracting the ratio of the mean tumor size of the test group relative to the control group from one and multiplying the result by 100.

The results of several experiments in mice bearing the 6C3HED lymphosarcoma when the instant compounds were administered orally are provided in the following table. In this table, column 1 gives the example number of the compound of Formula I administered; column 2 gives the dosage level of the compound in milligrams per kilogram of body weight; column 3 describes the percent inhibition of tumor growth; and column 4 tallies the number of mice which died during the course of the experiment relative to the total number of animals in the group.

| Example No. | Dosage | Percent Inhibition | Toxic/Total |
|---|---|---|---|
| 6 | 150 | 100 | 5/8 |
|   | 80 | 96 | 0/10 |
|   | 40 | 53 | 0/10 |
|   | 20 | 7 | 0/10 |
|   | 10 | 0 | 0/10 |
| 8 | 160 | 100 | 1/10 |
|   | 80 | 93 | 0/10 |
|   | 40 | 45 | 0/10 |
|   | 20 | 45 | 0/10 |
|   | 80 | 98 | 0/8 |
|   | 40 | 92 | 0/8 |
| 3 | 300 | 28 | 3/10 |
|   | 150 | 28 | 0/10 |
| 1 | 150 | 84 | 4/10 |
| 4 | 150 | 48 | 1/10 |
| 5 | 300 | 100 | 0/10 |
|   | 150 | 84 | 1/10 |
| 13 | 80 | 44 | 0/8 |
|   | 40 | 8 | 0/8 |
| 11 | 300 | 66 | 8/10 |
|   | 150 | 47 | 2/10 |

-continued

| Example No. | Dosage | Percent Inhibition | Toxic/Total |
|---|---|---|---|
| 12 | 300 | 69 | 0/10 |
|  | 150 | 43 | 0/10 |
| 9 | 300 | 57 | 2/9 |
|  | 150 | 26 | 0/10 |
| 10 | 300 | 80 | 0/10 |
|  | 150 | 37 | 0/10 |
| 7 | 300 | 100 | 1/10 |
|  | 150 | 84 | 0/10 |
| 2 | 300 | 37 | 0/10 |
|  | 150 | 11 | 0/10 |

The Formula I compounds are usually administered in the form of pharmaceutical compositions, preferably orally. Such compositions are prepared in a manner well known in the pharmaceutical art and comprise at least one active compound.

The present invention also includes pharmaceutical compositions which contain, as the active ingredient, the compounds of Formula II associated with pharmaceutically acceptable carriers In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 600 mg/kg of body weight. In the treatment of adult humans, the range of about 1 to about 50 mg/kg, in single or divided dose, is preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way.

Formulation 1

Hard gelatin capsules containing the following ingredients are prepared:

| Ingredient | Quantity (mg/capsule) |
|---|---|
| N-[[(3,4-dichlorophenyl)amino]carbonyl]-benzo[B]thiophene-5-sulfonamide | 250.0 |
| Starch | 305.0 |
| Magnesium stearate | 5.0 |

The above ingredients are mixed and filled into hard gelatin capsules in 560 mg quantities.

Formulation 2

A tablet formula is prepared using the ingredients below:

| Ingredient | Quantity (mg/tablet) |
|---|---|
| N-[[(4-chlorophenyl)amino]carbonyl]-5-benzofuransulfonamide | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

| Ingredient | Weight % |
|---|---|
| N-[[(3,4-difluorophenyl)amino]carbonyl]-2-benzofuransulfonamide | 5 |
| Lactose | 95 |

The active mixture is mixed with the lactose and the mixture is added to a dry powder inhaling appliance.

Formulation 4

Tablets, each containing 60 mg of active ingredient, are prepared as follows:

| Ingredient | Quantity (mg/tablet) |
|---|---|
| N-[[(3-chloro-4-trifluoromethylphenyl)amino]-carbonyl]-6-benzofuransulfonamide | 60.0 mg |
| Starch | 45.0 mg |

| Ingredient | Quantity (mg/tablet) |
| --- | --- |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5

Capsules, each containing 80 mg of medicament are made as follows:

| Ingredient | Quantity (mg/capsule) |
| --- | --- |
| N-[[(3,4-dichlorophenyl)amino]carbonyl]benzo[B]thiophene-5-sulfonamide | 80.0 mg |
| Starch | 109.0 mg |
| Magnesium stearate | 1.0 mg |
| Total | 190.0 mg |

The active ingredient, cellulose, starch, and magnesium stearate are blended, passed through a No. 20 mesh U.S. sieve, and filled into hard gelatin capsules in 190 mg quantities.

Formulation 6

Suppositories, each containing 225 mg of active ingredient are made as follows:

| Ingredient | Amount |
| --- | --- |
| N-[[(3,4-dichlorophenyl)amino]carbonyl]-6-benzofuransulfonamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspension, each containing 50 mg of medicament per 5.0 mL dose are made as follows:

| Ingredient | Amount |
| --- | --- |
| N-[[(4-methylphenyl)amino]carbonyl]-benzo[B]thiophene-5-sulfonamide | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor | q.v. |
| Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of medicament, are made as follows:

| Ingredient | Quantity (mg/capsule) |
| --- | --- |
| N-[[(4-trifluoromethylphenyl)amino]carbonyl]-6-benzofuransulfonamide | 150.0 mg |
| Starch | 407.0 mg |
| Magnesium stearate | 3.0 mg |
| Total | 560.0 mg |

The active ingredient, cellulose, starch, and magnesium stearate are blended, passed through a No. 20 mesh U.S. sieve, and filled into hard gelatin capsules in 560 mg quantities.

We claim:

1. A compound of the formula

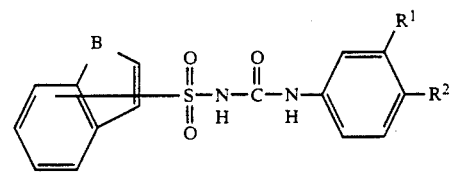

wherein:

B is —O—, or —S—;

$R^1$ is halo, $C_1$-$C_3$ alkyl, or hydrogen; and $R^2$ is halo, $C_1$-$C_1$ alkyl, or trifluoromethyl, or a pharmaceutically acceptable salt or solvate thereof.

2. A compound according to claim 1 wherein $R^1$ is hydrogen.

3. A compound according to claim 2 wherein $R^2$ is halo.

4. A compound according to claim 3 wherein the compound is N-[[(4-chlorophenyl)amino]carbonyl]-6-benzofuransulfonamide.

5. A compound according to claim 3 wherein the compound is N-[[(4-chlorophenyl)amino]carbonyl]-5-benzofuransulfonamide.

6. A compound according to claim 3 wherein the compound is N-[[(4-chlorophenyl)amino]carbonyl]benzo[B]thiophene-3sulfonamide.

7. A compound according to claim 3 wherein the compound is N-[[(4-chlorophenyl)amino]carbonyl]benzo[B]thiophene-2-sulfonamide.

8. A compound according to claim 3 wherein the compound is N-[[(4-chlorophenyl)amino]carbonyl]-4-benzofuransulfonamide.

9. A compound according to claim 1 in which $R^1$ is chloro, fluoro or bromo.

10. A method of treating susceptible neoplasms is mammals which comprises administering to a mammal in need of said treatment an oncolytically effective amount of a compound of the formula

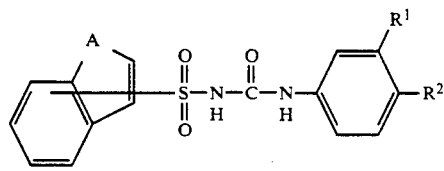

wherein:
A is —O—, —NH—, or —S—;
$R^1$ is halo, $C_1$–$C_3$ alkyl, or hydrogen; and
$R^2$ is halo, $C_1$–$C_3$ alkyl, or trifluoromethyl
or a pharmaceutically acceptable salt or solvate 11. A method of claim 10 employing a compound wherein R; is hydrogen.

12. A method of claim 11 employing a compound wherein $R^2$ is halo or trifluoromethyl.

13. A method of claim 11 employing a compound wherein $R^2$ is chloro, fluoro, or trifluoromethyl.

14. A method of claim 11 employing a compound wherein $R^2$ is chloro or fluoro.

15. The method of claim 14 employing N-(4-chlorophenyl)amino]carbonyl]-6benzofuransulfonamide.

16. The method of claim 14 employing N-(4-chlorophenyl)amino]carbonyl]-5-benzofuransulfonamide.

17. The method of claim 14 employing N-[[(4-chlorophenyl)amino]carbonyl]-4-benzofuransulfonamide.

18. The method of claim 14 employing N-[[(4-chlorophenyl)amino]carbonyl]benzo[B]thiophene-3-sulfonamide.

19. The method of claim 14 employing N[[(4-chlorophenyl)amino]carbonyl]benzo[B]thiophene-2-sulfonamide 20. The method of claim 14 employing N[[(4-chlorophenyl)amino]carbonyl]-1H-indole-6-sulfonamide.

21. The method of claim 14 employing N[[(4-chlorophenyl)amino]carbonyl]-1H-indole-6-sulfonamide.

22. The method of claim 14 employing N[[(3,4-dichlorophenyl)amino]carbonyl]-5-benzofuransulfonamide.

23. A pharmaceutical formulation comprising an effective amount of a compound of the formula

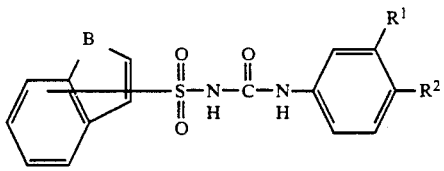

wherein:
B is —O— or —S—;
$R^1$ is halo, $C_1$–$C_3$ alkyl, or hydrogen; and
$R^2$ is halo, $C_1$–$C_3$ alkyl, or trifluoromethyl,
or a pharmaceutically acceptable salt or solvate thereof, in combination with a suitable pharmaceutical excipient.

24. A formulation according to claim 23 employing a compound wherein $R^1$ is hydrogen.

25. A formulation according to claim 23 employing a compound wherein $R^2$ is halo.

26. A formulation according to claim 24 employing a compound wherein $R^2$ is halo.

27. A formulation according to claim 26 employing N-[[(4-chlorophenyl)amino]carbonyl]-6-benzofuransulfonamide.

28. A formulation according to claim 26 employing N-[[(4-chlorophenyl)amino]carbonyl]-5-benzofuransulfonamide.

29. A formulation according to claim 26 employing N-[[(4-chlorophenyl)amino]carbonyl]-4-benzofuransulfonamide.

30. A formulation according to claim 26 employing N-[[(4-chlorophenyl)amino]carbonyl]benzo[B]thiophene-3-sulfonamide.

31. A formulation according to claim 26 employing N-[[(4-chlorophenyl)amino]carbonyl]benzo[B]thiophene-2-sulfonamide.

32. A formulation according to claim 26 employing N-[[(4-chlorophenyl)amino]carbonyl]-1H-indole-6-sulfonamide.

33. A formulation according to claim 26 employing N-[[(4-chlorophenyl)amino]carbonyl]-1H-indole-6-sulfonamide.

34. A formulation according to claim 26 g N-[[(3,4-dichlorophenyl)amino]carbonyl]-5-benzofuransulfonamide.

* * * * *

UNITED STATES PATENT AND TRADEMARK OFFICE
CERTIFICATE OF CORRECTION

PATENT NO. : 5,169,860

DATED : December 8, 1992

INVENTOR(S) : Fariborz Mohamadi et al.

It is certified that an error appears in the above-identified patent and that said Letters Patent is hereby corrected as shown below:

Column 4, line 44, "from C up to" should read -- from about 0°C up to. --

Column 4, line 45, "temperature C to about" should read -- temperature of about 20°C to about. --

Column 9, line 11, "bromobenzofuran. followed by" should read -- bromobenzofuran. Metallation of the 2-trimethylsilyl-6-bromobenzofuran, followed by. --

Column 9, line 34, "-indolesulfonamide" should read -- 2-indolesulfonamide. --

Column 11, line 53, "mouse tumors in" should read -- mouse tumors in vivo. --

Column 18, line 47, "1H-indole-6-sulfonamide" should read -- 1H-indole-2-sulfonamide. --

Column 18, line 49, "claim 26 g" should read --claim 26 employing. --

Signed and Sealed this

Fifth Day of September, 1995

Attest:

BRUCE LEHMAN

Attesting Officer

Commissioner of Patents and Trademarks